(12) United States Patent
Pomatto et al.

(10) Patent No.: US 6,340,353 B1
(45) Date of Patent: Jan. 22, 2002

(54) MANUFACTURE OF CRANIAL REMODELING ORTHOSIS

(76) Inventors: Jeanne K. Pomatto, 7665 E. Larkspur, Scottsdale, AZ (US) 85260; R. Craig Pomatto, 4215 N. Civic Center Blvd., #253, Scottsdale, AZ (US) 85251

( * ) Notice: Subject to any disclaimer, the term of this patent is extended or adjusted under 35 U.S.C. 154(b) by 0 days.

(21) Appl. No.: 08/720,528

(22) Filed: Sep. 30, 1996

(51) Int. Cl.[7] ............................ A61F 5/00; G06F 19/00
(52) U.S. Cl. ......................... 602/17; 700/118; 700/182
(58) Field of Search .................... 364/474.24, 474.03; 602/17, 5; 395/121; 600/587; 356/601, 607–608; 345/420–421; 446/391; 700/182, 118

(56) References Cited

U.S. PATENT DOCUMENTS

| | | | | | |
|---|---|---|---|---|---|
| 4,302,097 A | * | 11/1981 | Chlestil | ..................... | 355/52 |
| 4,633,416 A | * | 12/1986 | Walker | ..................... | 395/131 |
| 4,638,798 A | * | 1/1987 | Sheldon et al. | ............. | 606/130 |
| 4,737,921 A | * | 4/1988 | Goldwasser et al. | ......... | 395/124 |
| 4,791,934 A | * | 12/1988 | Brunnett | ..................... | 128/653 |
| 4,821,200 A | * | 4/1989 | Oberg | ..................... | 364/474.24 |
| 4,835,688 A | * | 5/1989 | Kimura | ..................... | 395/124 |
| 5,094,229 A | * | 3/1992 | Pomatto et al. | ............... | 602/17 |
| 5,280,305 A | * | 1/1994 | Monroe et al. | ......... | 446/391 X |
| 5,308,312 A | * | 5/1994 | Pomatto et al. | ............... | 602/17 |
| 5,342,202 A | * | 8/1994 | Deshayes | ..................... | 434/270 |
| 5,522,402 A | * | 6/1996 | Cooley | ..................... | 128/782 |
| 5,539,649 A | * | 7/1996 | Walsh et al. | ........... | 364/474.05 |
| 5,596,503 A | * | 1/1997 | Flint | ..................... | 446/391 X |
| 5,683,243 A | * | 11/1997 | Andreiko et al. | ............. | 433/3 |
| 5,867,588 A | * | 2/1999 | Marquardt | ................. | 382/118 |
| 5,951,498 A | * | 9/1999 | Arnett | ..................... | 600/587 |

* cited by examiner

*Primary Examiner*—Denise Pothier
(74) *Attorney, Agent, or Firm*—Donald J. Lenkszus

(57) ABSTRACT

A system and methods for the production of cranial remodeling orthoses are described. The patient's head is scanned to produce three dimensional data. The scanned data is modified to produce data which is representative of a preferred head shape. The preferred head shape data is used to produce a custom cranial remodeling orthosis for the patient.

10 Claims, 5 Drawing Sheets

| | |
|---|---|
| PATIENT NO. 1 | 2000 |
| PATIENT DATA-SCAN 1 | 2001 |
| SCAN DATA FILE-SCAN 1 | 2002 |
| CORRECTIVE SHAPE- SCAN 1 | 2003 |
| CORRECTIVE SHAPE (EXPERT)-SCAN 1 | 2004 |
| ORTHOSIS DESIGN- SCAN 1 | 2005 |
| | 2000a |
| PATIENT DATA – SCAN 2 | 2001a |
| SCAN DATA FILE-SCAN 2 | 2002a |
| CORRECTIVE SHAPE- SCAN 2 | 2003a |
| CORRECTIVE SHAPE (EXPERT)-SCAN 2 | 2004a |
| ORTHOSIS DESIGN- SCAN 2 | 2005a |
| | |
| PATIENT NO. 2 | 2020 |
| " | |
| " | |
| " | |
| " | |
| " | |
| " | |
| " | |
| " | |
| " | |
| " | |
| PATIENT NO. N | |

FIG. 2

MANUFACTURE OF CRANIAL REMODELING ORTHOSIS

FIELD OF THE INVENTION

This invention pertains to a system and method for the manufacture of cranial remodeling orthoses for correction of cranial abnormalities.

BACKGROUND OF THE INVENTION

An infant's head is commonly misshapen as a result of head molding from the birthing process. The shape gradually improves to a normal shape within the first six weeks of life. However, many infants, i.e., approximately one in 250, exhibit abnormal head shape which without intervention does not return to normal shape.

One such abnormal head shape is known as positional plagiocephaly. Infants with positional plagiocephaly may exhibit complex multistructural asymmetry affecting the cranial vault, face and skull base or facial expression. These head shape deformations may result from environmental factors such as premature birth, restrictive intrauterine environment, birth trauma, cervical anomalies, sleeping position, lack of full bone mineralization, neurological deficits or from the interaction of any of these or other factors.

Surgery of the cranial vault is a commonly used treatment for significant plagiocephaly. However, it has been difficult with surgery to obtain the desired permanent correction in growing infants. As a result of these difficulties, external orthotic devices have been developed which can be used to provide non-invasive, non-surgical correction of cranial abnormalities. Such orthoses have been developed to correct plagiocephaly as well as other cranial abnormalities such as brachycephaly and scaphocephaly. The orthosis device takes advantage of the growing, soft skull of an infant. The orthosis device restrains growth at the protusions in the skull and allows for growth where needed.

In our prior U.S. Pat. No. 5,094,229 issued Mar. 10, 1992, for "CRANIAL REMODELING ORTHOSIS" and U.S. Pat. No. 5,308,312 issued May 3, 1994, for "CRANIAL REMODELING ORTHOSIS" we described non-invasive orthosis devices which are of thermoplastic construct comprised of a semi-rigid styrene outer shell thermobonded to a medium durometer polyurethane foam inner lining.

In the past, others have attempted to develop and utilize standardized, off the shelf types of orthoses. It is our belief that the current state of such standardized orthoses is such that they do not represent a desired approach to the correction of highly individualized and unique abnormalities. Because the abnormalities which are to be corrected are unique for each infant, standardized off-the-shelf cranial remodeling bands are ineffective for treatment of most cranial abnormalities.

We have determined that to be effective, the cranial remodeling device must be a custom device which is specially constructed for each infant patient. These devices are fabricated from a plaster of Paris impression taken from an infant patient's head. This impression or negative is filled with a plaster slurry to create a positive mold which is an exact reproduction of the infant's head. A highly talented and skilled orthotist or clinician then constructs a second or corrected head mold by filling in areas on the first mold to produce a mold which is of the desired head shape. The orthosis device is then created over the corrected mold. The correction included in forming the corrected mold is based on clinical experience as well as objective anthropomorphic measurements. In the process for producing orthosis devices described in the aforementioned patents, a highly skilled specialist, i.e., an orthotist, modifies the initial positive mold of the patient's head. The modifications are based in large part upon the specialist's experience and skill.

To obtain the desired cranial remodeling results requires a course of treatment in which may require fabrication of more than one orthosis for an infant patient. Various factors influence the decision to use more than one orthosis. These factors may include the age of the patient at the start of treatment, the degree of severity of cranial abnormality, and the rate of cranial growth. In addition, it may be necessary to change the initial orthosis design during the course of treatment. For instance, a helmet shaped orthosis may be used initially and the final orthosis may be in the shape of a band.

The technique of utilizing a plaster of paris impression of the patient's head provides an extremely accurate reproduction of the patient's head. However, the results of the technique are highly dependent on the skill of the specialist clinician.

In some instances, cranial remodeling orthoses may be utilized as a post surgical treatment.

It is one object of the present invention to provide a system and method which will make the availability of individually customized cranial remodeling orthoses much more widespread.

It is still a further object of the present invention to provide a system and method of fabricating orthoses in which the fabrication of the orthoses is less dependent upon the skill of an orthotist or clinician to produce acceptable results.

SUMMARY OF THE INVENTION

The foregoing and other objects are accomplished by the system and method of the present invention.

In a system in accordance with the principles of the invention, the patient's head is scanned utilizing a scanner. The scanner generates data representative of the surface shape of the patient's head.

In accordance with the invention, the scanned data is supplied to an automatic milling machine which will produce a positive mold of the patient's head from which the clinician can produce the corrected mold.

Alternatively, the scanner data can be used by a computer to generate a display of the scanned head in a three dimensional view on the computer display. A clinician can then modify the three dimensional graphic to produce a corrected image of the patient's head. The computer generated corrected image is then utilized to generate a data file. The data file may be transmitted to the milling machine to produce a corrected positive mold of the patient's head.

Alternatively, the data file may be utilized to produce the design of a cranial remodeling orthosis which will correct the cranial abnormality of the patient. Automated equipment is utilized to produce the orthosis based upon the information contained in the data file.

Still further in accordance with the principles of the invention, the computer operates on the scanned data along with client specific data which specifies anthropomorphic information relative to the patient. The computer generated data can be utilized to form a mold of the patient's head from which an orthosis can be molded, or the data can be utilized to control the operation of a fabrication apparatus which will directly produce the orthosis.

BRIEF DESCRIPTION OF THE DRAWING

The invention will be better understood from a reading of the following detailed description taken in conjunction with the drawing in which:

FIG. 2 is a representative memory map illustrating memory files and subfiles;

DETAILED DESCRIPTION

Figure 1:
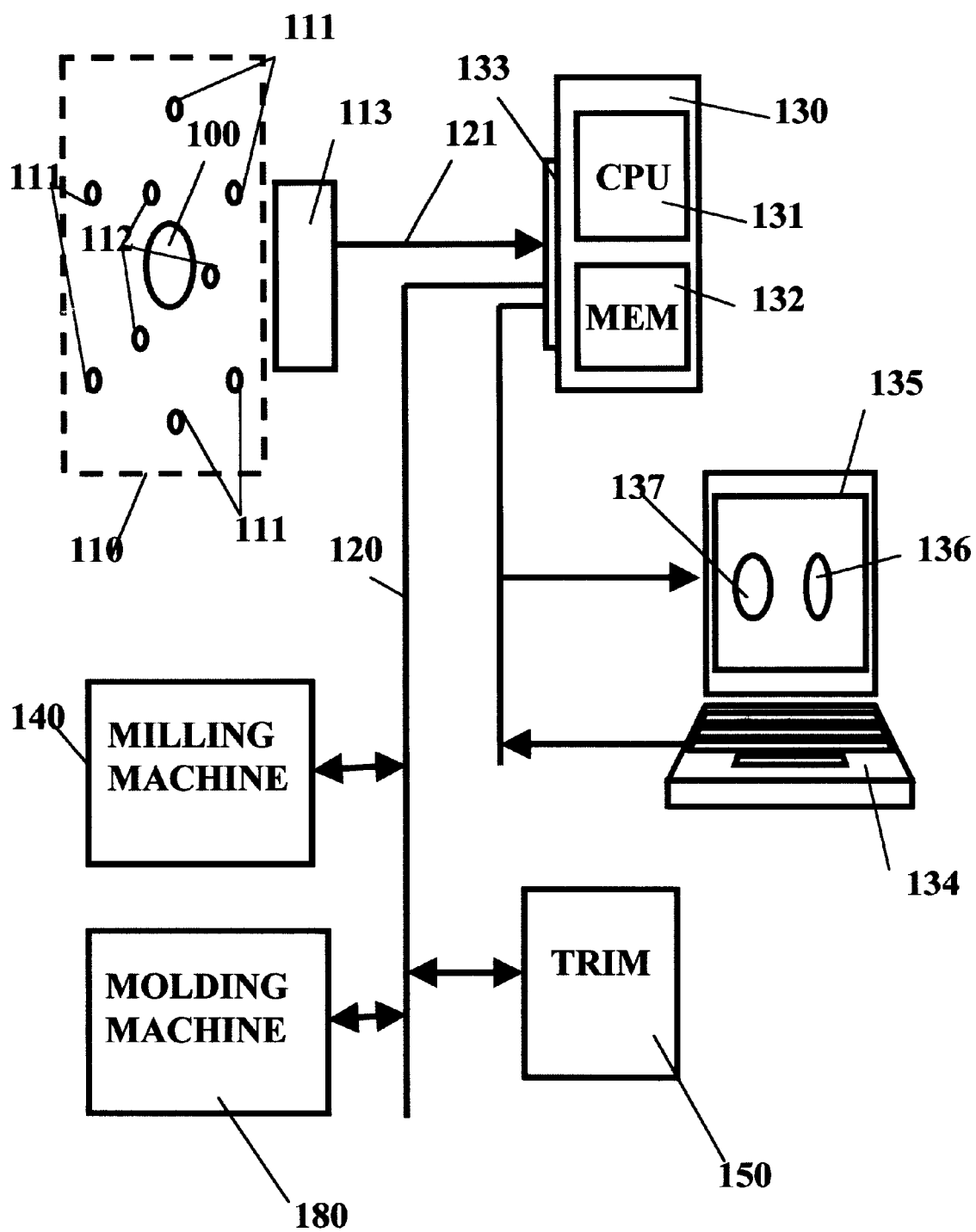
FIG. 1 illustrates in block diagram form the system apparatus for manufacturing cranial remodeling orthoses.

In the illustrative embodiment of the invention shown in FIG. 1, a scanner 110 is coupled to a computer 130 via an input/output port 133 of the computer 130. The scanner 110 is a laser scanner or other optical scanner of the type utilized in the scanning of humans. The scanner may be a three dimensional surface scanner of a type commercially available from Rose Imaging, Inc. or from Cyberware, Inc. The purpose of the scanner is to produce data from which a three dimensional representation of the patient's head may be generated.

The scanner 110 scans the patient's entire head. In contrast with certain prior scanners, which, for example, scanned only the face, it is important that the scanner utilized in the present invention scan the entirety of the head, including the top of the head. Therefore, it is important that the scanner 110 should include scanning elements to scan the top of the head. Thus, the scanner 110 is shown with several scanning devices 111 located in a plane disposed to produce a partial scan of the head 100 and additional scanning devices 112 positioned so that the top of the head 100 may be scanned. The scanner 110 includes a scan controller 113 which controls the scanning devices 111 and 112 and processes the scan data into an appropriate digital format.

In some instances, the scanner may be of the type utilized to produce cranial computed tomography (CT) also known as computerized axial tomography (CAT). Alternate imaging techniques such as nuclear magnetic resonancy or particle emission tomography may also be utilized. However, when utilizing tomographic scanners, the data produced will be utilized to generate three dimensional topographic data rather than the tomographic "slices" which are typical of these scanners. However, tomographic type of imaging systems in conjunction with software which will appropriately select and map data taken from the "slices" to produce a three dimensional data record may be more readily available.

Scanner 110 is used to scan the head 100 of a patient, typically an infant, having a cranial head shape abnormality, and thereby obtain data representing the patient's head shape. It is desirable that the scan of the head be completed in as short a time as possible. Typically, scanners which are utilized to scan three dimensional objects may scan 20,000 points on the object to be scanned. Scanning a large number of points increases the time required to complete the scan. For a conventional scanner, it may take 15 seconds or more to complete the three dimensional scan. Adequate scan results for purposed of cranial remodeling orthosis may be achieved with significantly fewer scan points. With approximately 1000 scan points adequate accuracy is obtained and the scan time is reduced to less than two seconds. A short scan time is significant because it is difficult to have an infant remain immobile for more than a few seconds at a time.

Scanner 110 transmits the head shape scan data over a link 121 to computer 130. The link 121 may be a direct connection to the input/output port 133 of the computer 130 or alternatively may be a modem connection to the computer 130. The computer may be any commercially available computer and may be at a different physical location than that of the scanner 110. Where the scanner 110 and the computer 130 are in separate locations, the data obtained from the scanner may be transmitted to the computer 130 via any available data transmission method and apparatus such as by modem and phone line, by computer diskettes, or other means.

Computer 130 is a commercially available computer of conventional configuration and includes a processor unit 131, memory 132 which may include RAM, disk, optical and other memory, input/output port 133 as well as human interfaces including a keyboard 134 or other input means and a display 135. Computer 130, after receiving scanned head shape data from scanner 110, stores the scanned data in a memory file or storage location that is uniquely identifiable and associated with the identity of the patient as well as other pertinent information about the patient.

Prior to scanning the patient's head, patient specific data is entered into the computer. The patient specific data includes identification information and also includes anthropomorphic information specific relative to the patient. For example, the patient's age, weight, height, sex, race and other characterizing features are entered and stored in the patient's data file.

Computer 130 also contains a data base stored in memory 132 which contains anthropomorphic data such as age, sex, race, height, weight and similar information which is of significance in determining an appropriate desired head shape. The computer also includes expert system software which will utilize the anthropomorphic data in conjunction with the patient specific data and the scan data to design an appropriate orthosis device.

FIG. 2 illustrates the manner in which patient information is stored in memory 132. The memory includes files which are specific to the patient. In FIG. 2, the file 2000 for a patient identified as Patient No. 1 is shown. It should be appreciated that the system of the present invention will have stored in memory patient files for numerous patients.

Patient specific data for Patient No. 1 which is entered into the system is stored in a patient subfile 2001. During a course of treatment of a patient, the patient's head will be scanned at periodic intervals and the Patient specific data entered for each scan will be entered into a different subfile. The scan data for Patient #1 obtained for the first scan is stored in Scan Data subfile 2002. As explained below, the clinician may provide modifications to the scan data to develop a corrective shape. The corrective shape data is stored in subfile 2003. Also, the computer 130 utilizes expert system software and anthropomorphic data stored in a database which is not shown in the drawing can generate a corrective shape. The expert system generated data is stored in subfile 2004. The orthosis design for the patient may also be generated by computer 130. The design data is stored in subfile 2005.

During the course of treatment, the patient's head will be scanned at periodic intervals and new data will be generated. For each patient scan, the computer 130 will store information into additional subfiles 2000(a) through 2000(n), thus monitoring a complete history for the patient. Files will normally be set for other patients.

The computer 130, using commercially available software, converts preferred head shape data into digital machine commands transmitted over bus 120 to a commercially available milling machine 140 that utilizes such digital machine commands to produce an exact positive mold of the patient's preferred head shape. The clinician can then utilize the positive mold to manually produce a cranial remodeling orthosis. Alternatively, the orthosis data may be directly provided to a molding machine 180 which directly produces the orthosis.

The machines 140 and/or 180 may be located in proximity to the computer 130 and/or the scanner 110 or it may be physically remote from one or the other or both. The data representative of either the positive form of the desired head shape or representative of the orthosis may be transmitted to the machines 140 and/or 180 in any conventional manner. The transmission of data from the computer 130 to the machines 140 and/or 180 may be programmed to occur automatically by computer 130 or may require manual initiation.

Machine 140 may be the commercially available milling machine referred to by the trademark name The Seattle Carver which is available from M+IND. Such a machine is adapted to receive digital data and convert the data into an exact plaster positive.

If the milling machine 140 is utilized to produce the positive mold, the orthosis device may be produced by utilizing the methods described in our aforementioned patents. After the resilient band is finished and cooled, it is trimmed utilizing a laser trimmer 150. Computer 130 transmits digital machine commands to laser trimmer 150, and the orthosis is trimmed along the trim lines specified by the data.

The trimmed orthosis is then taken from laser trimmer 150 and polished to produce a cranial remodeling orthosis that is ready to fit the patient whose head was scanned.

The system shown in FIG. 1 may be operated in several modes.

In a first mode of operation, the patient's head 100 is scanned by scanner 110. The computer 130 receives scan data from scanner 110 for a patient 100. The computer 130 converts the data into digital machine commands which are transmitted to milling machine 140. The milling machine 140 utilizes the digital machine commands to produce an exact positive mold of the patient's actual head shape.

Figure 3:
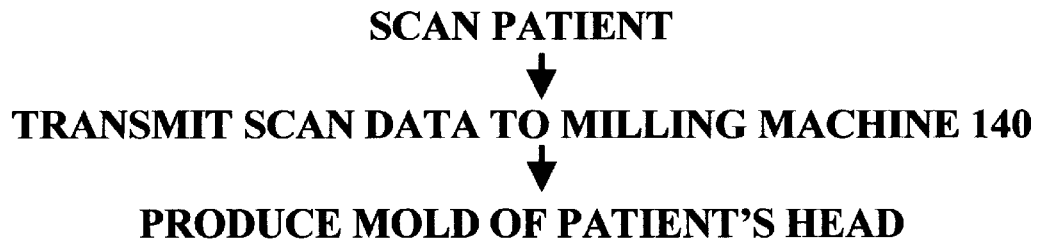
FIGS. 3, 4, and 5 are process flow diagrams.

The foregoing steps are shown in FIG. 3. The clinician may then produce a cranial remodeling orthosis device by manually modifying the positive mold to produce a second positive mold which is used to form the orthosis device.

The advantage of the first mode of operation is that the orthosis devices may be fabricated at a central location wherein the scanning of the patient may be performed at locations remote from the fabrication facility. Then the investment required to make the treatment available over a wide geographic area is decreased.

Figure 4:
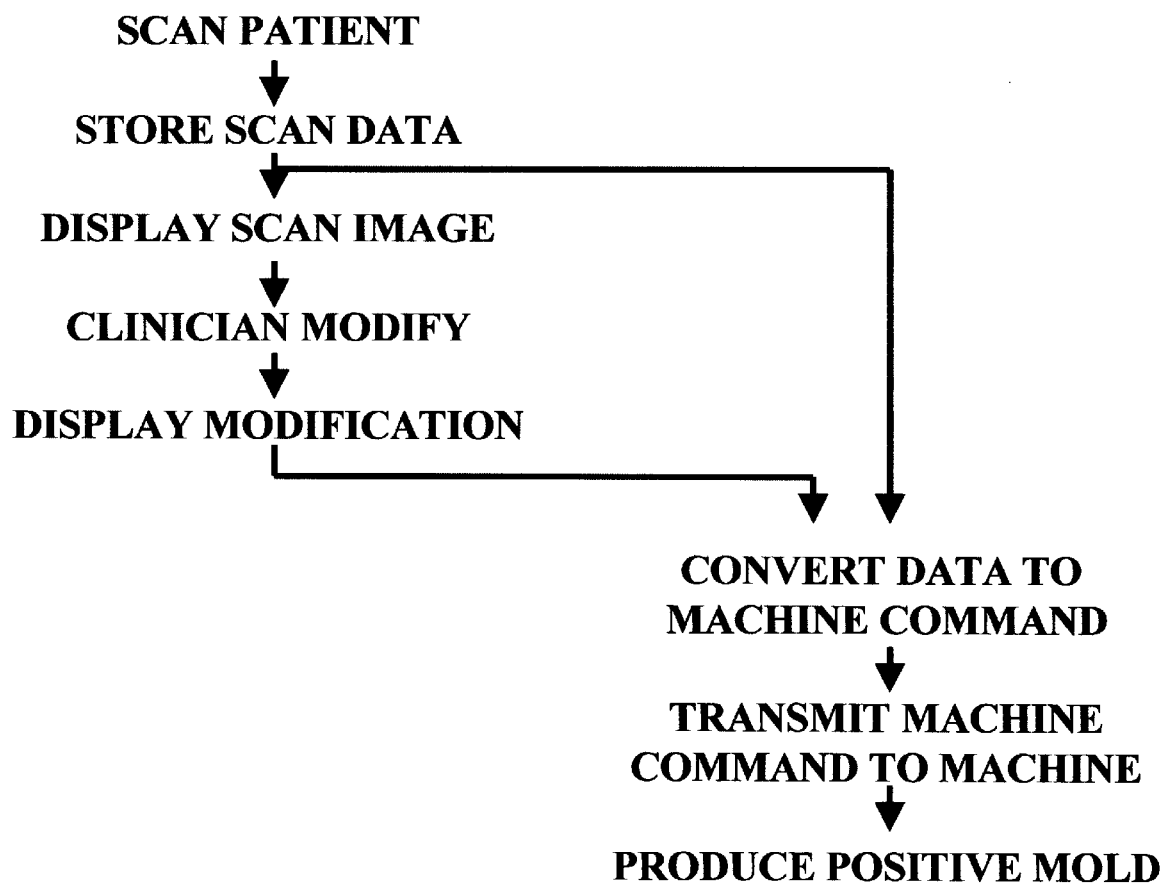

In a second mode of operation illustrated in FIG. 4, the computer 130 utilizes the scan data to display a three dimensional representative image of the patient's head on the display 135. Utilizing commercially available software the image 136 may be viewed from any perspective direction through rotation of the image. By viewing the image of the patient's head, the clinician may determine and display a desired head shape 137 correcting for the abnormalities. In addition, the clinician may view the anthropomorphic information to assist in making determinations of the desired head shape. The computer can display in three dimensions both the scanned image 136 of the patient's head and the corrected image 137 as determined by the clinician's modifications. The clinician may choose to utilize either image 136 or 137 as the desired image upon which to base the construction of the orthosis device. In either case, the clinician will determine a desired head shape image. The clinician may utilize the desired head shape image to assist in determining the actual head shape to which the orthosis should be conformed. In certain instances the clinician may determine that the correction should occur through the use of more than one orthosis during treatment of the patient's condition. In these instances, the clinician will be able to project the growth pattern of the patient and to develop designs for all the orthoses which will be utilized during the course of treatment.

The clinician uses commercially available image rectification software to manipulate the scanned head shape image, thereby producing new data and a new image representing the desired head shape for the patient. This manipulation is done by viewing the image of the actual head shape produced by the computer 130 and concomitantly changing the image into that of the desired head shape. The computer 130 translates the desired-head-shape image into desired-head-shape data.

Figure 5:
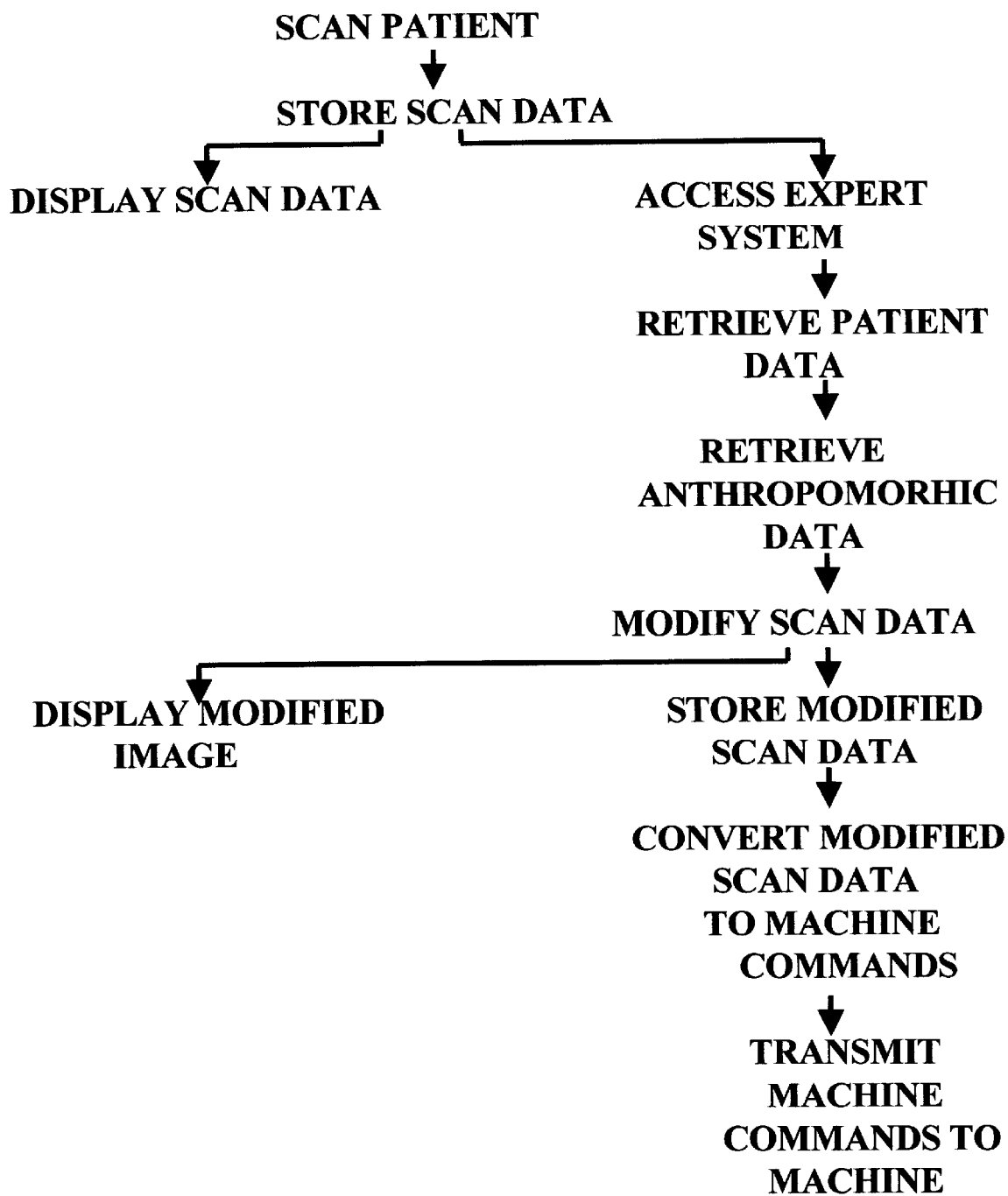
Figure 6:
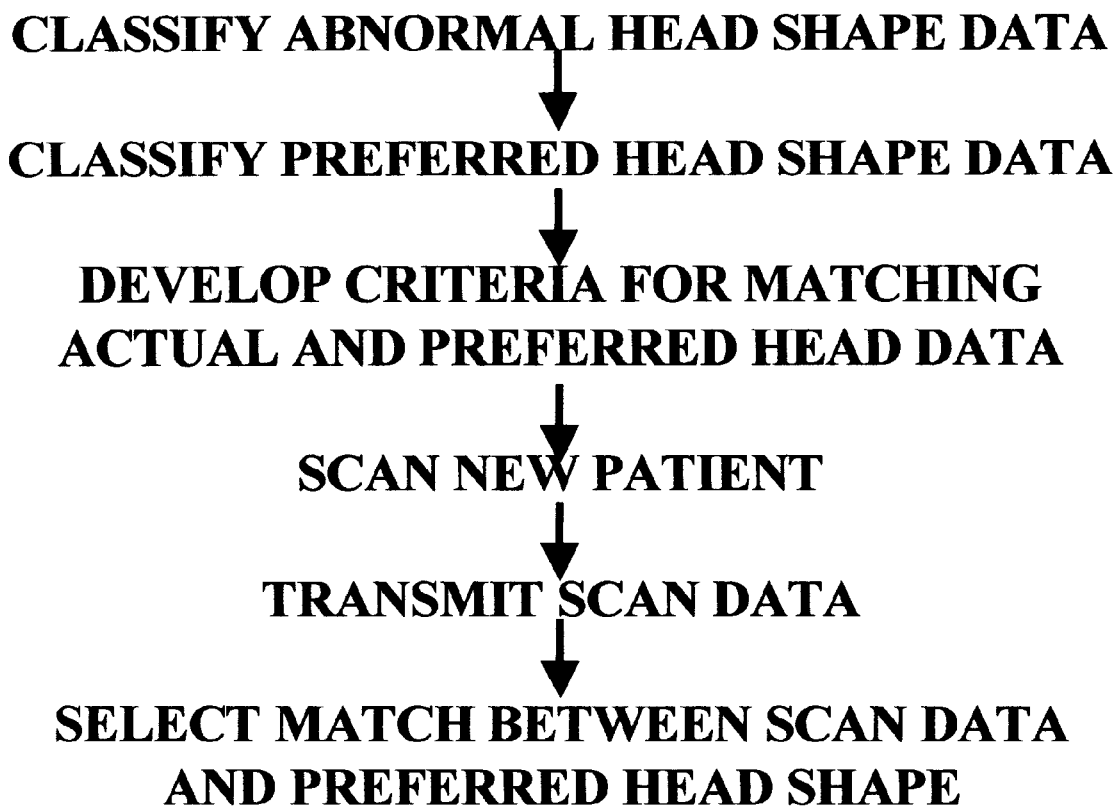
FIG. 6 is a flow diagram for an expert system.

In an additional mode of operation illustrated in FIG. 5, the clinician may also utilize the anthropomorphic information to have the computer generate an image of the desired head shape of the patient based upon the anthropomorphic information. The computer utilizes commercially available expert system software and is operated as an expert based system such that the computer 130 operates directly on the data representative of the patient's scanned head to produce data which is used to manufacture an orthosis. In this mode, the head shape scan data is received by the computer 130 from the scanner 110. In addition, an operator will enter patient specific anthropomorphic information. The patient specific information will be utilized to select anthropometric data from the anthropomorphic data base which will enable the computer to determine the desired head shape for that individual patient. The computer will then, at the selection of the operator, display both an image 136 of the patient's head as scanned and an image 137 of the patient's head as corrected. At this time, a clinician can view the images 136, 137 to verify that the computer has produced an appropriate desired head shape. Simultaneous with the display of the head images, the computer 130 will also display patient specific information as well as anthropomorphic information from which the desired head shape was produced. After verifying that the desired or preferred head shape is acceptable, the operator or clinician will command the computer 130 to store the desired head shape data into the computer's memory 132 in a storage location that is uniquely identifiable and associated with the identity of the patient.

In the event the clinician chooses to utilize the scanned image, the automatic milling machine 140 will produce a mold of the patient's head. In the event the clinician chooses to utilize the modified image, the automatic milling machine 140 produces the corrected mold from which the orthosis device may be constructed. Alternatively, the clinician may modify the image 137 produced by the expert system software. The expert system resident on the computer 130 is utilized to further facilitate the selection, design and fabrication of appropriate orthoses. A first classification protocol for abnormal head shapes is stored in a data base of the memory 132 of computer 130, along with patients' actual head shape data, along with race, sex, age, and other factors that influence selection of a preferred head shape. A second classification protocol is prepared that identifies desired head shape data based upon anthropometric data and other factors, and it is also stored on the computer memory. A correlation is then established that relates the first and second classification protocols. From the protocols and patient data, an orthosis type is selected and the specifications for the orthosis are generated.

When a new patient is examined, the head is scanned and head shape scan data is produced, as described above. Computer 130, being preprogrammed to utilize the criteria and first and second protocols, selects a closest match between the new actual head shape and a preferred head shape. Using the preferred head shape match, computer 130 informs an operator via computer display 135, of the identity of an orthosis designed for the selected preferred head shape.

After data representative of the desired head shape is produced, the system may be operated such that the clinician specifies the design of the cranial remodeling orthosis or the computer prepares the design. When the system is operated such that the clinician specifies the design of the orthosis, the clinician utilizes the scanned head image to identify and designates locations on the image of the scanned head which should be covered by of a cranial remodeling orthosis. The computer 130 will then superimpose on the images of the scanned head the design of a cranial remodeling orthosis. The clinician can at that time modify the shape of the orthosis displayed to, for example, provide for additional corrective remodeling.

Alternatively, the computer 130 utilizing the desired head shape data along with patient specific information can automatically produce the final design of an orthosis which will correct the scanned head shape into the desired head shape. The orthosis designed by the computer 130 may at the request of the computer operator be displayed. The orthosis can be displayed separate from the images of the scanned head shape and desired head shape or it can be displayed in conjunction with either or both.

The data representative of the shape of the orthosis is stored in the computer memory 132.

One advantage of using computer software to produce an image of a desired shape of a subject's head include that it is less dependant on the skill of the clinician, and it produces quantifiable shape changes. The scanning of a patient's head to produce a digital representation eliminates the need to build a negative mold of the patient's head, and the associated discomfort to a patient.

It will be apparent to those skilled in the art that various changes may be made to the system and methods shown and described herein without departing from the spirit or scope of this invention, and it is intended that the invention not be limited by the illustrative embodiment shown and described, but only be limited by the claims appended hereto.

What is claimed is:

1. A method for fabricating a cranial remodeling orthosis comprising the steps of:
    scanning a patient's head with a scanner, said scanner providing first digital data representing a three dimensional image of the patient's head including the top of the patient's head,
    providing said first digital data representing a three dimensional image of said patient's head, including the top of said head, to a computer,
    utilizing said computer to produce second digital data representing a modified and preferred three dimensional shape of said patient's head,
    converting digital data representing said preferred head shape into machine commands to a mold producing machine,
    transmitting said machine commands to said machine to cause said machine to produce a mold, and
    producing a cranial remodeling orthosis from said mold.

2. A method for producing a cranial orthosis for a patient, comprising:
    scanning the head of said patient to produce scan data representative of a three dimensional image of the head;
    automatically utilizing said data to produce a first three dimensional representation of the head including the top portion thereof;
    modifying said first representation to produce a second representation, said second representation being a desired corrected three dimensional shape for the head;
    utilizing said second representation to produce a corrective mold; and
    utilizing said mold to produce a cranial orthosis for the head.

3. A method for producing a cranial orthosis for a patient, comprising the steps of:
    scanning the head of the patient to produce scan data representative of a three dimensional image of substantially the entirety of the head including the top portion of the head, said scanning being performed without subjecting the head to distorting pressurization;
    storing said scan data in a memory;
    entering patient specific data into a memory;
    utilizing an expert system to modify said scan data in accordance with certain of said patient data to produce second data, said second data being representative of a desired corrected three dimensional image for the head; and utilizing said second data to produce a cranial orthosis for the head.

4. A method in accordance with claim 3, further comprising:
    accessing anthropomorphic data; and
    said expert system utilizing said anthropomorphic data to produce said second data.

5. A method in accordance with claim 4, comprising:
    displaying a first image of the head based upon said scan data.

6. A method in accordance with claim 5, comprising:
    displaying a second image based upon said second data.

7. A method in accordance with claim 6, comprising:
    said first and second images are displayed simultaneously.

8. A method in accordance with claim 4, comprising:
    automatically updating said anthropomorphic data to include portions of said patient specific data.

9. A method in accordance with claim 3, comprising:
    utilizing said second data to produce a positive mold, said positive mold being utilized to produce said orthosis.

10. A method in accordance with claim 9, comprising:
    utilizing said second data to control a milling machine to produce said positive mold.

* * * * *